United States Patent [19]

Schmidt

[11] Patent Number: 4,490,881
[45] Date of Patent: Jan. 1, 1985

[54] DUST EXHAUSTOR

[76] Inventor: Otto Schmidt, Julius-Hölder-Str. 12, 7000 Stuttgart 70, Fed. Rep. of Germany

[21] Appl. No.: 469,110

[22] Filed: Feb. 23, 1983

[30] Foreign Application Priority Data

Feb. 25, 1982 [DE] Fed. Rep. of Germany ....... 3206714

[51] Int. Cl.³ .............................................. A47L 5/38
[52] U.S. Cl. .................... 15/301; 55/385 A; 55/DIG. 18; 98/115.1
[58] Field of Search ................ 15/301, 345, 303, 310; 55/DIG. 18, 385 A; 98/115 R, 115 LH, 115 SB, 115 VM

[56] References Cited

U.S. PATENT DOCUMENTS

| | | | |
|---|---|---|---|
| 3,295,298 | 1/1967 | Mackey | 15/310 X |
| 3,559,383 | 2/1971 | McCabe | 98/115 LH X |
| 3,729,905 | 5/1973 | Diccianni | 98/115 LH X |
| 3,828,530 | 8/1974 | Peters | 55/DIG. 18 |
| 3,944,405 | 3/1976 | van Calsteren et al. | 98/115 LH X |
| 4,098,174 | 7/1978 | Landy | 98/115 LH X |
| 4,100,847 | 7/1978 | Norton | 98/115 LH X |

*Primary Examiner*—Chris K. Moore
*Attorney, Agent, or Firm*—Fred Philpitt

[57] ABSTRACT

There is described a dust exhaustor for a precision-mechanics work table which can be fitted as a ready-to-connect unit beneath the work top of a conventional work table. For this purpose, the housing is L-shaped, the suction opening being in the front end of the substantially horizontal leg of the housing and the large-surface outlet(s) being in the vertical leg of the housing. The housing bounds, in its installed position, the foot or knee region for the user of the work area.

6 Claims, 1 Drawing Figure

U.S. Patent  Jan. 1, 1985  4,490,881
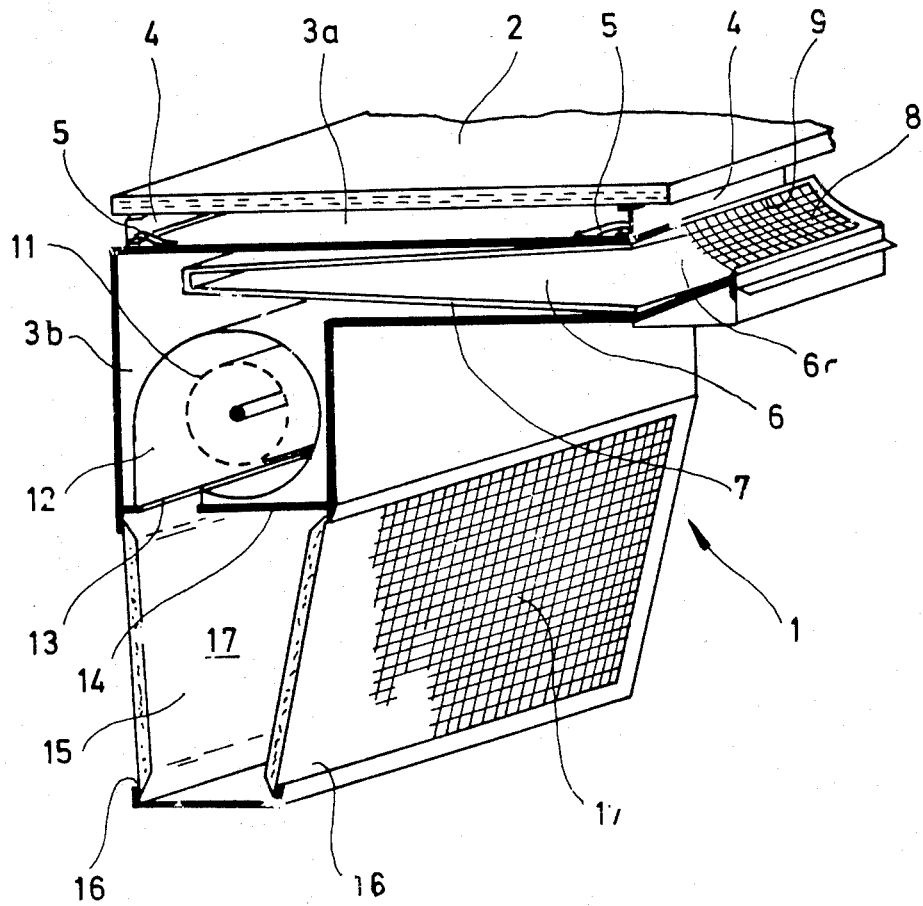

DUST EXHAUSTOR

The invention relates to a dust exhaustor for a precision-mechanics work table, comprising a slowly running low-pressure blower which, at the suction side, communicates with a large-surface suction opening through a suction channel and, at the pressure side, feeds the sucked-in air to at least one large-surface outlet through an outlet channel.

In dentistry, there occurs a considerable aerosol formation during the working of denture blanks, particularly during milling and grinding. The aerosol consists of flour of gypsum from dental impressions, rubber and plastics particles from the prosthesis bodies, abrasive grains and polishing agents of the grinding and polishing tools, gold and cobalt-chromium alloy particles from fillings, crowns and braces as well as of plastics material and rubber vapours which are formed when the workpieces and the grinding and polishing tools are heated. These disturbing substances are not only a great hindrance during work, because they lead to the obstruction of vision, a nuisance caused by smell, difficulty in breathing and a pollution of the work area, but also endanger health. Furthermore, for economic reasons it is necessary to bring about the greatest possible recovery of gold and to keep the energy consumption low. The latter fact means, above all, that the room air sucked in together with the dust has to be returned into the work area after appropriate filtering, so as to save the heating energy contained in the room air.

A dust exhaustor of the kind mentioned at the beginning is described in DE OS No. 29 13 871. In contrast to older constructions, wherein use is made of a fast-running industrial vacuum cleaner, a slow-running low-pressure blower is used herein. The field of suction is made so large that, due to the long sojourn time of the particles to be sucked off in the field of suction, reliable sucking is brought about despite the low air flow velocity. The air that has been sucked in by the low-pressure blower and has been purified by a filter is returned into the work room through large-surface outlets.

In this known construction, it was necessary to adapt the work table completely, in other words in its whole design, to the suction device. This meant that the price of such a suction table was very high and that, in particular, the conversion of existing laboratories to up-to-date suction equipment was rendered difficult.

It is the object of the present invention to develop a dust exhaustor of the kind mentioned at the beginning at a lower cost.

According to the invention, this problem is solved in that the dust exhaustor is designed as a ready-to-connect unit which can be fitted as a whole beneath the work top of conventional work tables and, for this purpose, has a substantially L-shaped housing, in which all the devices and assemblies required for the operation of the exhaustor are combined, the housing comprising:

(a) a leg which, in the installed position, is substantially horizontal and at the front end of which that is directed towards the user there is provided the suction opening, (b) a leg which, in the installed position, is substantially vertical and at the external surface of which there is (are) provided the outlet(s).

According to the invention, the dust exhaustor therefore is a unit which is entirely separate from the work table and which is assembled at the factory and is delivered in a ready-to-connect manner. Such dust exhaustors allow both existing work areas to be readily converted and new work areas to be set up for the first time. Thus, there do not arise any costs for a special design of the work table itself. Since the development according to the invention renders unnecessary individual constructions which are adapted to the respective work table, relatively large numbers of pieces are attainable, which render possible a cheaper production.

Up to the present invention, the integration of the exhaustor into the work table itself was considered to be necessary because one was of the opinion that, in order to reduce the velocity of the air flow emerging from the outlets, the size of the outlets would have to be such that they could only be provided on the external surfaces of the entire work table. The present invention is thus based on the realisation that it is possible for a satisfactory exhaustion to reduce the quantity of air sucked in to such an extent that an adequate number of outlets can be provided in the relatively small surface of the substantially vertical housing leg according to the present invention. This realisation is all the more surprising because, in the conception according to the invention, the outlets are disposed in the foot zone of the work table user, where health risks and feelings of indisposition are particularly liable to occur.

Expediently, the horizontal housing leg encloses the suction channel, this latter then comprising an inlet zone which extends towards the user side obliquely to the front and upwardly. This ensures that, in spite of the dust exhaustor being fitted beneath the work top, the suction opening will be directly beneath the front edge of the work top. Its field of suction can then become particularly effective at this point.

The vertical housing leg may be subdivided, by a partition wall, into an upper zone, in which the low-pressure blower is arranged, and a lower zone, in which the outlet channel extends.

All the lateral surfaces of the lower zone of the vertical housing leg may be provided with outlets. Meant by lateral surfaces are both the front directed towards the user and the rear directed away from the user and the right-hand and left-hand lateral surfaces of the lower housing leg, as viewed by the user. This arrangement is expedient even if the rear of the work table is placed against a wall.

If the vertical housing leg of the dust exhaustor according to the invention does not stand on the floor but the entire unit is fastened to the connection plate so as to be suspended therefrom, it is also possible to provide the lower front surface of the vertical housing leg with an outlet. This further increases the surface provided for the outlets and thus reduces the risk of locally high and unpleasant flow velocities of the exhaust air arising.

An exemplified embodiment of the invention will hereinafter be explained in more detail with reference to the drawing; the single FIGURE shows perspectively and in section an exhaustor according to the invention beneath a conventional, partially shown work top.

The exhaustor is marked in the FIGURE as a whole with the reference symbol 1. It is pre-fabricated as a unit and is moved as such beneath the work top 2 of a conventional work table and is fastened to this top. In its housing 3, there are combined all the devices and assemblies which are necessary for the operation of the exhaustor 1.

The housing 3 is substantially L-shaped and comprises a leg 3a, which is substantially horizontal in the installed position, and a substantially vertical leg 3b.

The horizontal leg 3a of the housing 3 has been fastened beneath the work top 2, for example by means of the shown profiled bars or dogs 4 and straps 5, in such a way that its underside bounds the foot or knee region for the work area user in the upward direction. In a corresponding manner, the side of the vertical housing leg 3b that is to the right in the drawing, and is thus directed towards the user, bounds the foot or knee region to the front.

The horizontal housing leg 3a encloses a suction channel 6, in which a dust filter bag 7 is accommodated. At the side that is directed towards the user, the suction channel 6 has an inlet zone 6a which extends obliquely to the top. By this means, the suction opening 9, which is covered by a grating 8, comes to lie a short distance beneath the front edge of the work top 2 when the exhaustor has been installed. Beneath the obliquely extending part of the suction channel inlet zone 6a, a waste drawer is accommodated in known manner.

In the upper part of the vertical housing leg 3b, there is accommodated a slow-running low-pressure blower, whose rotor 11 and air baffle plate 12 are diagrammatically indicated in the drawing. The low-pressure blower communicates at the suction side with the suction channel 6. The sucked-in air is ejected into an outlet channel 15 through an opening 13 in a housing intermediate wall 14.

The outlet channel 15 guides the air from the low-pressure blower to large-surface outlets 16 which are preferably provided in all the lateral surfaces of the vertical housing leg 3a, namely in the front that is directed towards the user, the rear that is directed away from the user and the lateral surfaces which are to the right and left, as viewed by the user. If the lower end 17 of the vertical housing leg 3a does not stand on the floor of the room, then another outlet 16 may be provided herein. The outlets 16 are each covered with a dust filtering layer 17, a super-fine filter of Class C.

Due to the described arrangement, there is brought about, not only in the zone of the suction opening 9, a largely laminar, irrotational flow which forms an extensive field of suction around the workpiece which has been worked on the work top 2 or on a filling board fastened thereto and not shown. Because of the relatively long sojourn time of the dust particles in this field of suction, this field is so effective, even if the flow velocity is relatively low, that it is capable of grasping fast flying particles. Nevertheless, the air ejected via the outlet 16, and which emerges in the foot region of the user, is virtually not felt.

In addition to the individual most important components described above, the housing 3 of the exhaustor 1 of course comprises all the other devices which are required or only expedient for the operation thereof, namely, in particular, the electric motor for the low-pressure blower, the electric control for this motor as well as any additional adjustable air baffle plates in the inlet zone 6a of the suction channel 6 which allow the suction field to be individually set in front of the suction opening 9. The exhaustor 1 is supplied from the factory ready to be connected, for example with a conventional power cable and power plug, so that it can be immediately put into operation after having been installed beneath the work top 2 of a conventional work table.

I claim:

1. A dust exhaustor for a precision-mechanics work table, comprising a slowly running low-pressure blower which, at the suction side, communicates with a large-surface suction opening through a suction channel and, at the pressure side, feeds the sucked-in air to at least one large-surface outlet through an outlet channel, characterized in that it is designed as a ready-to-connect unit which can be fitted as a whole beneath the work top (2) of conventional work tables and for this purpose, has a substantially L-shaped housing (3), in which all the devices and assemblies which are required for the operation of the exhaustor (1) are combined, the housing (3) comprising:
    (a) a leg (3a) which, in the installed position, is substantially horizontal and at the front end of which that is directed towards the user there is provided the suction opening (9),
    (b) a leg (3b) which in the installed position is substantially vertical and at the external surface of which there is provided at least one outlet, filter means in at least one of said legs for removing dust from the air flowing therethrough, and
    (c) a suction channel enclosed by said horizontal housing leg (3a), said suction channel having an inlet zone (6a), which extends towards the user side obliquely to the front and top.

2. A dust exhaustor as claimed in claim 1, characterised in that the vertical housing leg (3b) is subdivided by a partition wall (14) into an upper zone, in which the low-pressure blower (11, 12) is arranged, and a lower zone, in which the outlet channel (15) extends.

3. A dust exhaustor as claimed in claim 2, characterised in that all the lateral surfaces of the lower zone of the vertical housing leg (3b) are provided with outlets (16).

4. A dust exhaustor as set forth in claim 1 wherein the lower face of the vertical housing leg (3b) is provided with an outlet (16).

5. A dust exhaustor as set forth in claim 2 wherein the lower face of the vertical housing leg (3b) is provided with an outlet (16).

6. A dust exhaustor as set forth in claim 3 wherein the lower face of the vertical housing leg (3b) is provided with an outlet (16).

* * * * *